(12) United States Patent
Torp

(10) Patent No.: US 7,559,896 B2
(45) Date of Patent: Jul. 14, 2009

(54) PHYSIOLOGICAL DEFINITION USER INTERFACE

(75) Inventor: Anders Herman Torp, Oslo (NO)

(73) Assignee: General Electric Company, Schenectady, NY (US)

(*) Notice: Subject to any disclaimer, the term of this patent is extended or adjusted under 35 U.S.C. 154(b) by 489 days.

(21) Appl. No.: 11/212,214

(22) Filed: Aug. 26, 2005

(65) Prior Publication Data

US 2006/0058623 A1     Mar. 16, 2006

Related U.S. Application Data

(60) Provisional application No. 60/605,322, filed on Aug. 27, 2004.

(51) Int. Cl.
    *A61B 8/00*     (2006.01)
(52) U.S. Cl. ........................................ 600/443; 600/450

(58) Field of Classification Search ................. 600/450, 600/443; 382/128
See application file for complete search history.

(56) References Cited

U.S. PATENT DOCUMENTS 6,491,636 B2 * 12/2002 Chenal et al. ............... 600/450

* cited by examiner

*Primary Examiner*—Eric F Winakur
*Assistant Examiner*—Lawrence N Laryea
(74) *Attorney, Agent, or Firm*—Dean D. Small; The Small Patent Law Group

(57) ABSTRACT

A medical imaging system includes image acquisition circuitry, a display, and a processor coupled to the image acquisition circuitry and the display. In addition, a memory is coupled to the processor and stores a user interface program that causes the processor to display a physiological marker on the display, receive a control input directed to the physiological marker; and adjust the physiological marker in response to the control input.

23 Claims, 5 Drawing Sheets

PHYSIOLOGICAL DEFINITION USER INTERFACE

CROSS REFERENCE TO RELATED APPLICATIONS

The present application relates to, and claims priority from, provisional application Ser. No. 60/605,322, filed Aug. 27, 2004, and entitled "Physiologic Definition User Interface", the complete subject matter of which is hereby incorporated by reference in its entirety.

BACKGROUND OF THE INVENTION

1. Field of the Invention

This invention relates generally to medical imaging systems. More specifically, this invention relates to methods and systems in medical imaging systems that provide a user interface to help define and quantify physiological features.

2. Related Art

Doctors and technicians commonly use medical imaging systems to obtain, display, and study images for diagnostic purposes. In ultrasound imaging systems, for example, a doctor may obtain heart images in an attempt to learn whether the heart functions properly. In recent years, these imaging systems have become very powerful, and often include sophisticated measurement and analysis (M&A) subsystems. The M&A subsystems provide assistance in obtaining and determining diagnostic data from the images, such as heart rate, blood velocity, and physiological structure depth.

For certain examinations the M&A subsystem took initial steps to analyze and obtain diagnostic data from the images. However, the M&A subsystem typically lacked the doctor's expertise in identifying physiological structures (e.g., a heart valve) and events (e.g., ventricle diastole). Thus, the M&A subsystem typically could not be relied upon to find or identify many different physiological structures. As a result, manual input, without any initial guidance, was often required to define those structures.

In that regard, however, the sophistication of the M&A subsystems has sometimes rendered them difficult and complex to use and understand. Thus, interaction with the M&A subsystems has not always been as simple, fast, and easy as desired. As a result, it has been more cumbersome than necessary to analyze and obtain diagnostic data from the images.

Therefore, there is a need for overcoming the difficulties set forth above and others previously experienced.

BRIEF DESCRIPTION OF THE INVENTION

In one implementation, a medical imaging system includes image acquisition circuitry, a display, and a processor coupled to the image acquisition circuitry and the display. In addition, a memory is coupled to the processor and stores a user interface program that causes the processor to perform a method. The method includes the steps of displaying a physiological marker on the display, receiving a control input directed to the physiological marker; and adjusting the physiological marker in response to the control input.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the user interface. In the figures, like reference numerals designate corresponding parts throughout the different views.

DETAILED DESCRIPTION

Figure 1:
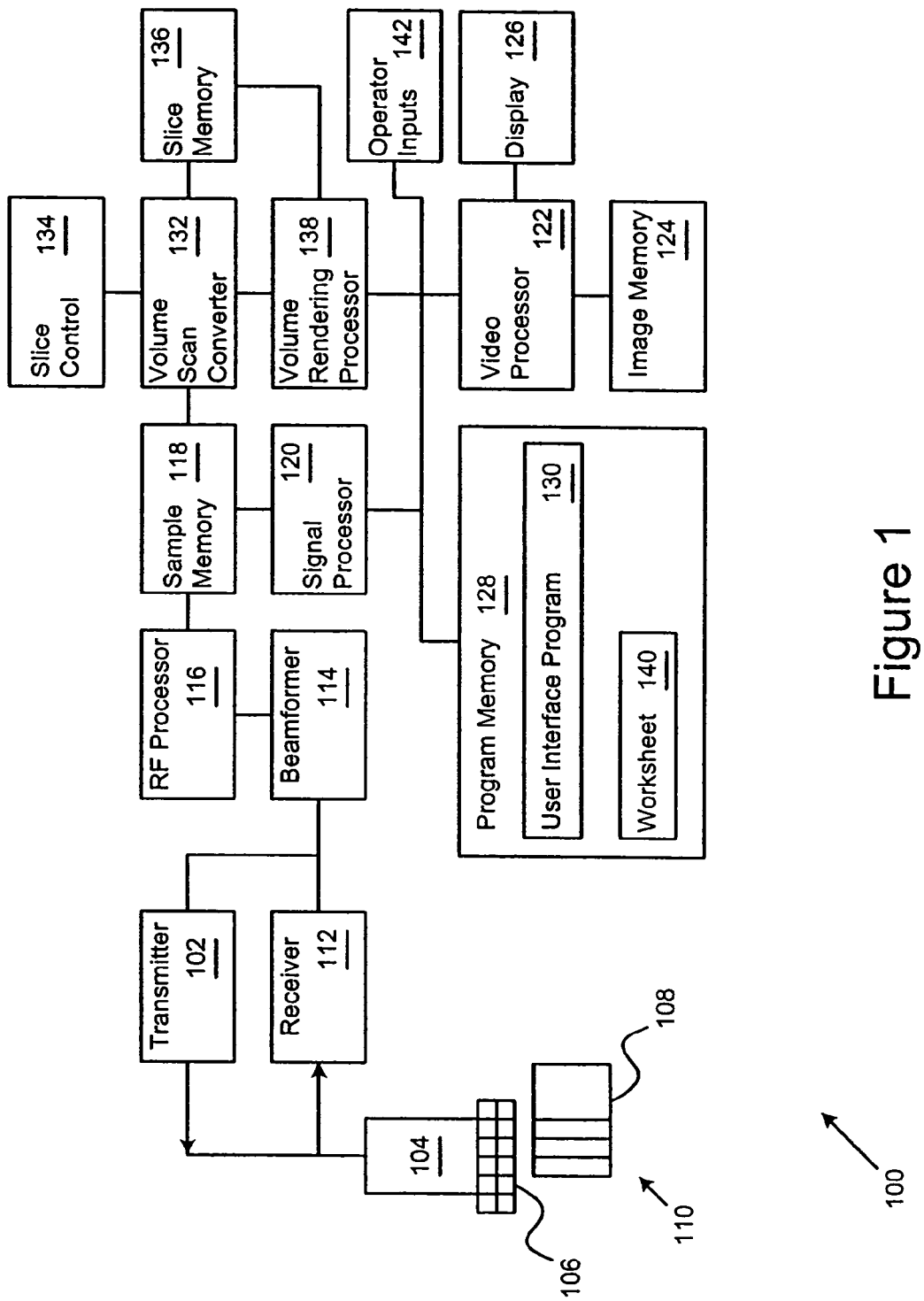
FIG. 1 illustrates an ultrasound imaging system suitable for use with the user interface discussed below.

Before turning in detail to the user interface systems and methods, an exemplary ultrasound imaging system suitable for employing the user interface is summarized with reference to FIG. 1. The invention is not limited to use with ultrasound systems, however, and may instead find use in a wide variety of imaging systems in which physiological structure is displayed, including X-ray systems, fluoroscopic systems, and the like.

FIG. 1 illustrates a diagram of the functional blocks of an ultrasound system 100. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the user interface program may be a separate stand alone program, one or more routines in one or more programs, may be implemented as functions in an operating system, subroutines or functions in an installed imaging software package, and the like.

Furthermore, the memories 118, 124, 128, 136 are not limited to any particular type or form. Rather, one skilled in the art will appreciate that all or part of the memories may be one or more types of signal bearing machine readable media including hard disks, floppy disks, CDs, a signal received from a network, RAM, DRAM, SDRAM, EPROM, EEPROM, Flash memory or other forms of RAM or ROM. Similarly, the processors may be microprocessors, microcontrollers, application specific integrated circuits, discrete logic or other types of circuits acting as processors.

The ultrasound system 100 includes a transmitter 102 which drives an ultrasound probe 104. The ultrasound probe 104 includes multiple transducers 106 that emit pulsed ultrasonic signals into a region of interest 108 (e.g., a patient's chest). In some examinations, the probe 104 may be moved over the region of interest 108 in order to acquire image information in scan planes 110 of the region of interest 108.

The probe 104 may conform to one of many geometries, as examples, a 1D, 1.5D, 1.75D, or 2D probe. Structures in the region of interest 108 (e.g., a heart, blood cells, muscular tissue, and the like) back-scatter the ultrasonic signals. The resultant echoes return to the transducers 106.

In response, the transducers 106 generate electrical signals that the receiver 112 receives and forwards to the beamformer 114. The beamformer 114 processes the signals for steering, focusing, amplification, and the like. The RF signal passes through the RF processor 116 or a complex demodulator (not shown) that demodulates the RF signal to form in-phase and quadrature (I/Q) data pairs representative of the echo signals. The RF or I/Q signal data may then be routed directly to the sample memory 118 for temporary storage.

The ultrasound system 100 also includes a signal processor 120 to process the acquired ultrasound information (i.e., the RF signal data or IQ data pairs) and prepare frames of ultrasound information (e.g., graphical images) for display. To that end, the signal processor 120 may provide the ultrasound information to the video processor 122. The video processor 122 stores frame data in the image memory 124, and outputs the video signals that drive the display 126. The display 126 may be, as examples, a CRT or LCD monitor, hardcopy device, or the like.

The signal processor 120 executes instructions out of the program memory 128. The program memory 128 stores, for example, an operating system for the ultrasound system 100, image processing programs, and (as will be explained in detail below), a user interface program 130 (UIP 130) and a worksheet 140. In general, the signal processor 120 performs any selected processing operation available on the acquired ultrasound information chosen from the configured ultrasound modalities present in the imaging system 100. The signal processor 120 may process in real-time acquired ultrasound information during a scanning session as the echo signals are received. Additionally or alternatively, the ultrasound information may be stored temporarily in the sample memory 118 during a scanning session and processed in less than real-time in a live or off-line operation.

The ultrasound system 100 may acquire ultrasound information at a selected frame rate (e.g., 50 frames per second) and display those frames at the same or different frame rate on the display 126. The memories shown in FIG. 1 may store processed frames that are not scheduled for immediate display. For example, the image memory 124 may be sized to store several seconds or more of image frames.

In addition or alternatively, the ultrasound system 100 may scan a volume from the region of interest 108. To that end, the probe 104 may be used in conjunction with techniques including 3D scanning, real-time 3D imaging, volume scanning, 2D scanning with transducers having positioning sensors, freehand scanning using a voxel correlation technique, 2D or matrix array transducers and the like.

When the probe 104 moves, as examples, along a linear or arcuate path, the probe 104 scans the region of interest 108. At each linear or arcuate position, the probe 104 obtains a scan plane from the region of interest 108. The scan planes 110 are collected to cover a selected thickness, for example, by collecting adjacent scan planes 110. The scan planes 110 are stored in the memory 118, and then passed to a volume scan converter 132. In some implementations, the probe 104 may obtain lines instead of the scan planes 110, and the memory 118 may store lines obtained by the probe 104 rather than the scan planes 110.

The volume scan converter 132 receives a slice thickness setting from a slice thickness selector 134 that an operator adjusts to choose the thickness of a slice to be created from the scan planes 110. The volume scan converter 132 creates a data slice from multiple adjacent scan planes 110. The number of adjacent scan planes 110 that form each data slice is dependent upon the thickness selected by the slice thickness selector 134. The data slice is stored in slice memory 136 for access by the volume rendering processor 138. The volume rendering processor 138, in conjunction with image processing programs in the program memory 128, performs volume rendering upon the data slice. The output of the volume rendering processor 138 passes to the video processor 122 and display 126.

The imaging system 100 responds to inputs provided by an operator through the operator inputs 142. The operator inputs may include, as examples, a keyboard, trackball, mouse, voice recognition, touchpad, buttons, touchscreen, and the like. As examples, the UIP 130 may assign any desired function to any of the keyboard keys, or display graphical buttons on the display 126 that the operator may select with a mouse-controlled cursor. The operator provides a control input to the UIP 130 when the operator activates any of the assigned keys or displayed buttons. The control input thus specifies that the operator has activated a given input. As will be explained in more detail below, the UIP 130 responds to the control inputs to perform certain physiological definition tasks.

In one mode of operation, the ultrasound system 100 displays sequences of images (e.g., B-mode images) captured by the probe 104, for example as cine-loops. One or more of the images may be displayed with physiologic markers under control of the UIP 130. As will be explained in more detail below, the UIP 130 allows an operator to define physiological structure (e.g., a ventricle), for example, as an aid in physiological quantification (e.g., determining an ejection fraction).

The UIP 130 will be described below with respect to obtaining physiological definitions for ejection fraction (EF) measurements. The ejection fraction is a measure that describes the percentage of blood pumped out of a ventricle during a cardiac cycle. For example, the left ventricle ejection fraction (LVEF) provides an indicator of left ventricular systolic function, and is typically defined as ((end-diastole volume)−(end-systole volume))/(end-diastole volume). The end-diastole volume is the left ventricular volume when the left ventricle is fully open (i.e., in the end-diastole state), while the end-systole volume is the left ventricular volume when the left ventricle is contracted to its greatest extent (i.e., in the end-systole state). It is noted, however, that the invention is not limited to ejection fraction measurements or physiology, but may be applied more generally to physiological definitions of many different types across numerous types of imaging systems.

Figure 2:
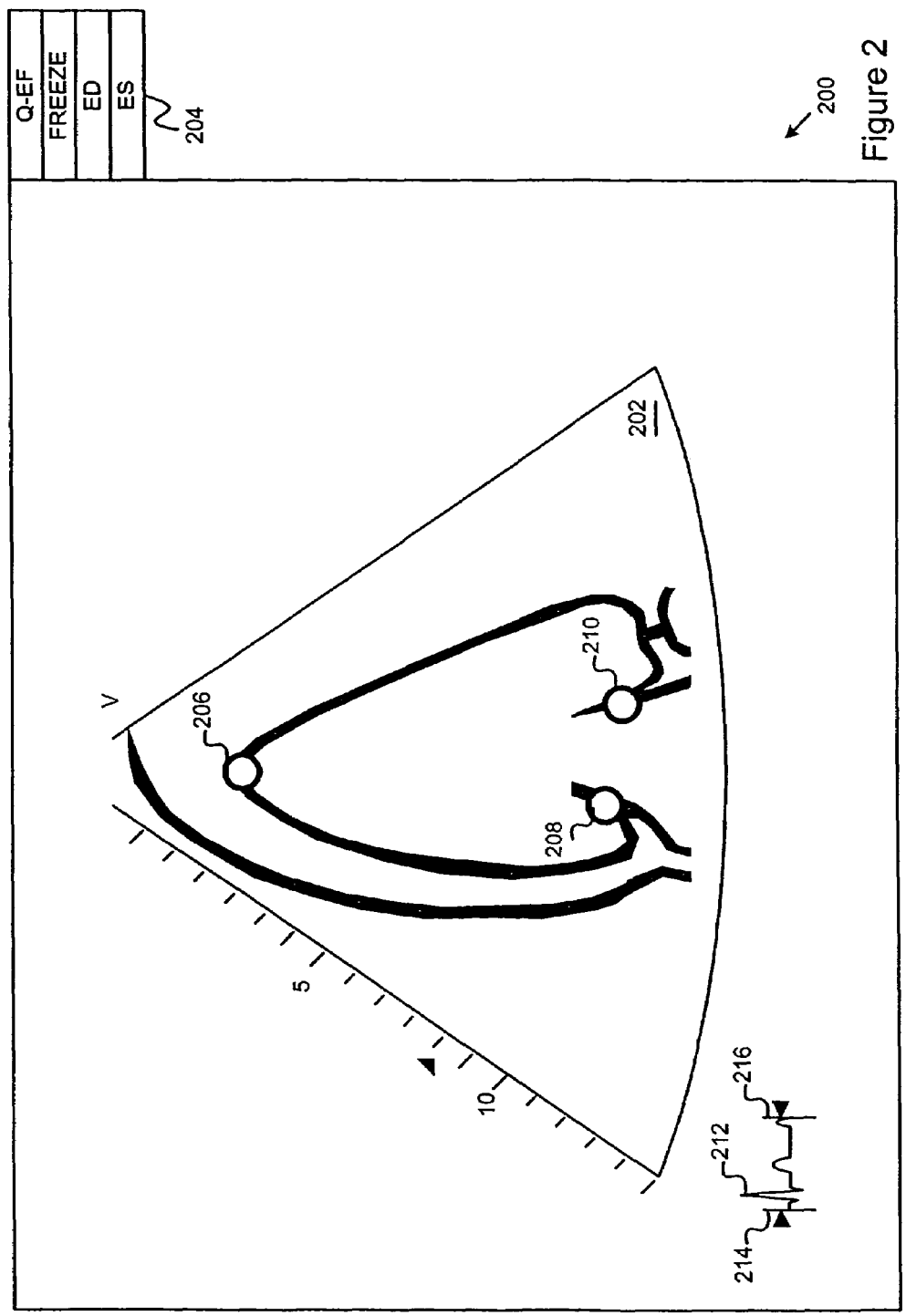
FIG. 2 depicts a B-mode image that the ultrasound imaging system shown in FIG. 1 has generated on a display attached to the imaging system.

Turning next to FIG. 2, that figure depicts a display screen 200 including a B-mode sector image 202 that the ultrasound imaging system 100 has generated on the display 126. The display screen 200 includes interface buttons that the UIP 130 draws on the screen as a menu 204 with selectable buttons. As shown in FIG. 2, the buttons include a Q-EF button, a FREEZE button, an ES (End Systole) button, and an ED (End Diastole) button. In one implementation, the operator provides control inputs through the menu 204 using a mouse, trackball, touchpad, keyboard, voice input, or the like. Thus, for example, the operator may use a mouse to move a pointer to a particular button, then click on a mouse button to select the button. In response, the UIP 130 receives a control input that indicates which button the operator has selected.

To begin preparing for ejection fraction measurements, the operator presses the Q-EF button. In response, the imaging system 100 obtains tissue velocity imaging (TVI) information from the patient. The imaging system 100 employs (e.g., through an M&A subsystem) the TVI information as an aid in determining where the ventricle apex (the top of the ventricle) is located, as well as where the mitral valve lies.

The UIP 130 subsequently displays physiological markers on the B-mode display 202 at the locations where the physiological structures were identified. In FIG. 2, for example, the UIP 130 displays a ventricle apex marker 206, a first mitral valve marker 208, and a second mitral valve marker 210. The markers 206-210 are circular markers, but other shapes, sizes, line weights, fill patterns, colors, animated, blinking or static graphics and the like may be employed instead.

The two mitral valve markers 208-210 together form a physiological marker for the atrio-ventricular (AV) plane. The AV plane is the plane defined by the mitral valve containing the wall separating the atrium from the ventricle.

The operator may visually inspect the placement of the markers 206-210 while adjusting the probe 104 or other settings to determine when the imaging system has approximately correctly determined the ventricle apex and the mitral valve. When the operator is satisfied, the operate may select the FREEZE button.

In response, the UIP 130 receives a control input that indicates that the FREEZE button has been pressed. The UIP 130 may then interact with the operator in order to help determine the LVEF. To that end, the imaging system 100 may display a cine-loop of left ventricle B-mode images such as those shown in FIG. 2 in slow motion (i.e., greater than zero frames per second, but less than real-time). The cine-loop may, for example, include image frames obtained at the same time as the ECG signal 212, with image frames displayed in time from a pre-selected start time 214 to a pre-selected end time 216 of the ECG signal 212.

Figure 3:
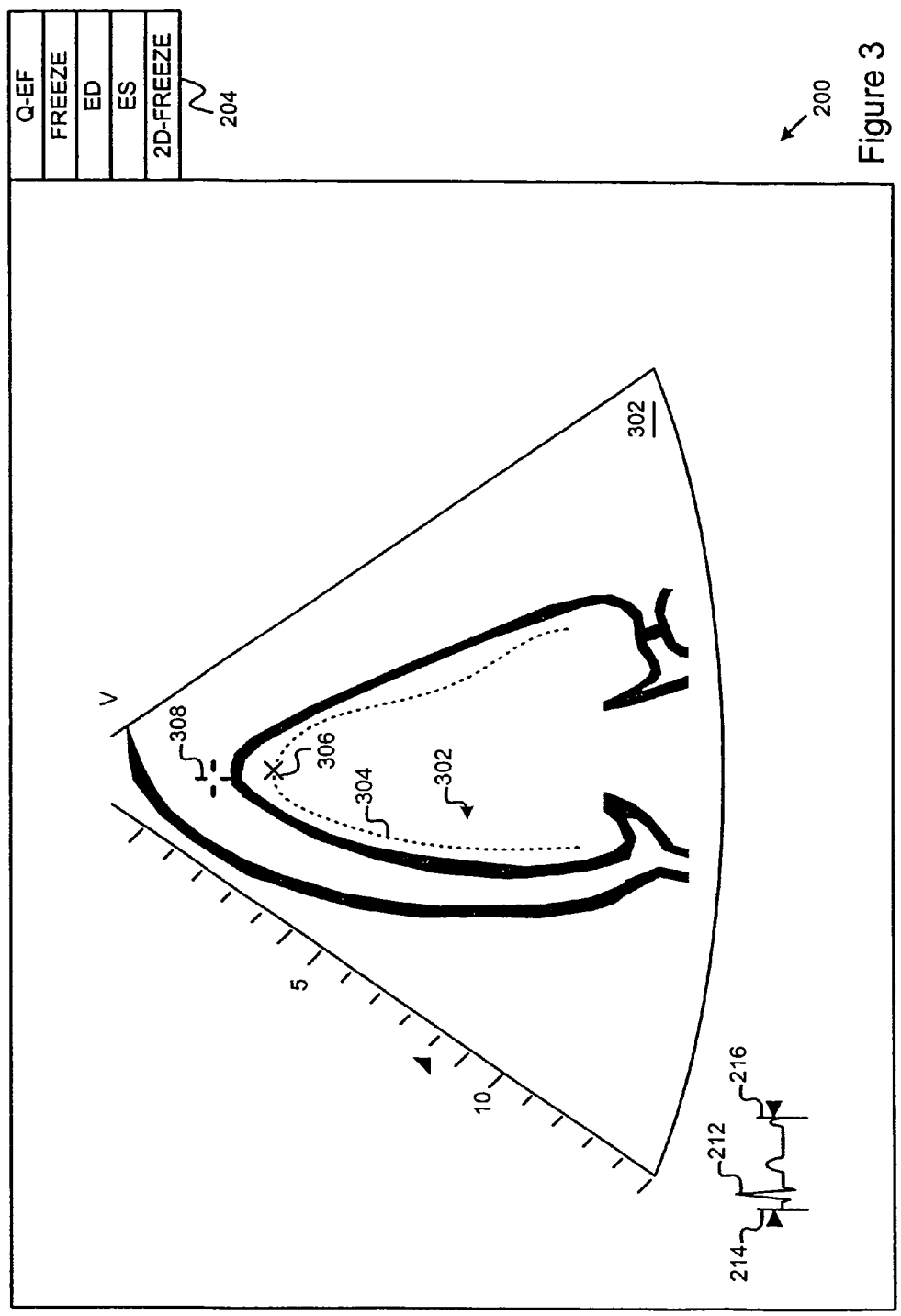
FIG. 3 shows a B-mode image including detected endocard that the ultrasound imaging system shown in FIG. 1 has generated on a display attached to the imaging system.

While displaying the cine-loop, the UIP 130 displays physiological markers on the display, as shown in FIG. 3. FIG. 3 shows the display screen 200, one B-mode frame 302 in the cine-loop, and new physiological markers drawn on the display. In particular, FIG. 3 shows a ventricle endocard 302 drawn with a contour line 304. A ventricle apex marker 306 marks the location of the ventricle apex, and a cursor 308 provides a visual pointer shape that the operator can move to select buttons, provide drawing input, positioning input, and the like as noted below.

A contour line is a graphical indicator of a physiological feature or landmark present in an image. The contour line makes identifying the location and shape of physiological landmarks easier for the operator. The ventricle endocard 302 is a graphical representation of the space occupied by the ventricle at any particular point in the cardiac cycle. The UIP 130 may obtain the spatial location information for drawing the endocard 302 from an automated physiological landmark detection procedure in an M&A subsystem, or from manual operator input, as examples.

As shown in FIG. 3, the endocard 302 is a two dimensional cross sectional area. The contour line 304 is a dashed line that traces the detected area occupied by the ventricle to form the endocard 302. Each frame in the cardiac cycle will show a detected endocard which will grow and shrink as the ventricle opens and closes.

The UIP 130 allows the operator to change the location of the ventricle apex by repositioning the ventricle apex marker 306. To that end, the UIP 130 accepts positioning control input in the form of a spatial location (e.g., an X-coordinate and Y-coordinate) for the cursor 308 and, for example, a mouse click that indicates that the operator desires to reposition the ventricle apex at the position of the cursor 308. In response, the UIP 130 repositions the ventricle apex marker 306 at the selected location. In addition, the UIP 130 sends the new ventricle apex location to an M&A subsystem, for example, an edge detection program, that determines the location of the ventricle walls. The M&A subsystem updates the spatial location information for the detected endocard and the UIP 130 redraws the endocard using that information.

Figure 4:
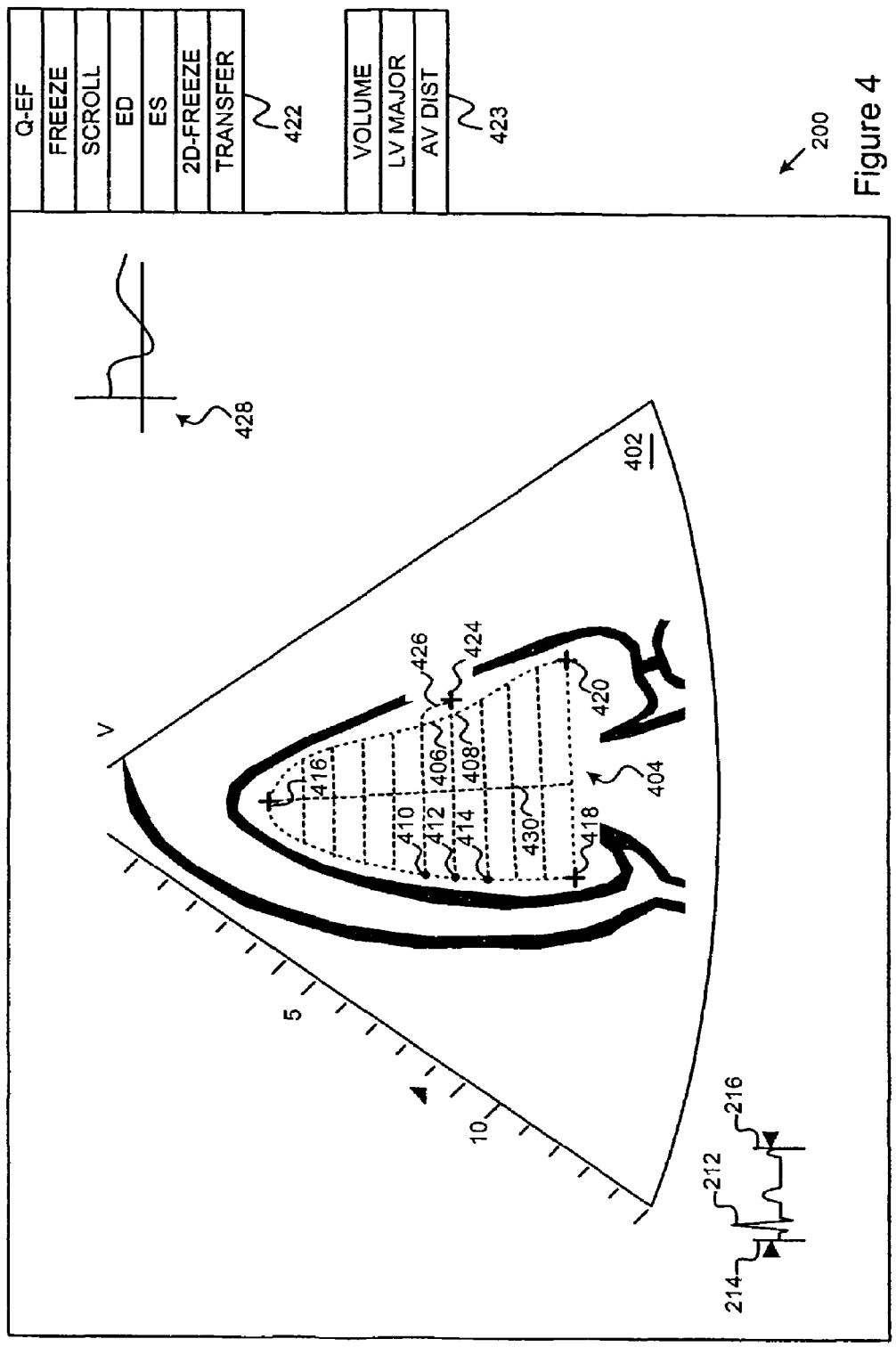
FIG. 4 illustrates a B-mode image including a segmented end-diastole endocard drawn on a B-mode image generated by the ultrasound imaging system shown in FIG. 1.

In one embodiment, once the operator is satisfied with the location of the ventricle apex marker 306, the operator may select the 2D-FREEZE button to freeze the cine-loop. In that event, as shown in FIG. 4, the UIP 130 will automatically display the end-diastole B-mode frame 402, and display the corresponding end-diastole endocard 404. The end-diastole endocard 404 is formed from multiple endocard segments (two of which are labeled 406, 408). In one implementation the endocard segments are line segments drawn between vertex points (such as the vertex points labeled 410, 412, and 414). The UIP 130 also draws the ventricle major axis 430 as well as a ventricle apex marker 416, and the AV plane markers 418 and 420.

The UIP 130 also displays a button menu 422 and a plot menu 423. The button menu 422 includes the Q-EF button, 2D-FREEZE button as well as the ED, ES, SCROLL, and TRANSFER A4C buttons that are explained below. The plot menu 423 includes the VOLUME button, LV MAJOR button and the AV DIST buttons that are also explained below. The UIP 130 displays the button menu 422 and the plot menu 423 on the display screen, and to select a button, the operator may move the cursor 308 over any of the buttons and click, or press an assigned keyboard key, or the like.

When the endocard 404 is on the display 126, the UIP 130 accepts drawing input from the operator. More particularly, the operator may use the mouse, trackball, keyboard, or the like to draw modifications to the endocard 404. Thus, as shown in FIG. 4, the operator moves the drawing cursor 424 to create the drawing input 426. The drawing input 426 is a new endocard segment for the endocard 404. In other words, the operator may adjust the automatically detected endocard 404 by drawing new endocard segments with the drawing cursor 424.

In one implementation, the UIP 130 accepts input from the operator in the form of a mouse click or other selection mechanism that selects one of the endocard segments. Then, the UIP 130 tracks the motion of the drawing cursor 424 to record the spatial positions that correspond to the drawing input 426. When the operator indicates that the drawing input 426 is complete (e.g., by clicking or releasing a mouse button), the UIP 130 replaces the selected endocard segment with a new endocard segment obtained through the drawing input 426.

In another implementation, the operator draws near the endocard segment that the operator desired to modify. In response, the UIP 130 changes the nearest endocard segments to reflect the drawing input. Thus, the operator may draw a complete contour that replaces all of the endocard segments.

Note also that the operator may move the ventricle apex and AV plane by clicking on the ventricle apex marker 416 or the AV plane markers 418-420 and moving them to a new location. The operator may, for example, click the mouse button to select the new location. In response, the UIP 130 repositions the markers that were moved, and, optionally, informs the M&A subsystem of the new locations so that it may re-determine the endocard.

Additionally, the operator may further change the B-mode frame in which the end-systole condition is detected. As noted above, when the operator presses the 2D-FREEZE button, the imaging system 100 automatically displays what it considers the end-systole B-mode frame 402. The operator may change the B-mode frame by selecting the SCROLL button and, for example, moving a trackball forward or back to advance or regress through B-mode frames. The UIP 130 will fade out the detected end-systole contour 404 to indicate that a new B-mode frame is being considered for the end-systole image.

When the operator has found the B-mode frame that shows the end-systole condition, the operator draws a segment of the endocard as noted above. Alternatively, the operator may draw a complete contour that replaces all of the endocard segments. In response, the imaging system 100 marks the current B-mode frame as the end-systole B-mode frame, while the UIP 130 replaces one or more endocard segments, or a complete contour according to the drawing input.

The operator may then select the ED button to direct the UIP 130 to switch to the end-diastole frame. In response the UIP 130 displays the B-mode image containing the end-diastole frame, and displays the end-diastole endocard. The explanation provided above with regard to the end-systole endocard applies to the manipulation of the end-diastole endocard. Thus, as examples, the UIP 130 may draw the end-diastole endocard with end-diastole endocard segments and may accept input from the operator to modify one or more of the segments, the complete contour, the ventricle apex marker, and AV plane markers, and the like.

The button menu 422 includes the TRANSFER button to provide the operator with a mechanism for providing a completion input to the UIP 130. When the operator is satisfied with the endocards, the operator clicks the "TRANSFER" button. In response, the UIP 130 initiates transfer of endocard measurements to the worksheet 140. The worksheet 140 is a general storage area in memory for physiological measurements. The M&A subsystem may then retrieve data stored in the worksheet 140, for example, to calculate the LVEF.

More specifically, the UIP 130 may store (or initiate storage of) an end-systole volume or endocard area and an end-diastole volume or endocard area to the worksheet 140. The volumes may be extrapolated from the detected endocard areas for each frame of the cardiac cycle by the UIP 130, or by separate M&A subsystem procedures.

When the operator clicks on one of the buttons in the plot menu 423, the UIP 130 responds by drawing the indicated plot, for example, in the upper right hand corner of the display. As an example, the operator may click on the VOLUME button, and in response, the UIP 130 will display a plot of ventricle volume as a function of time. Similarly, when the operator presses the LV MAJOR button, the UIP 130 will display a plot of the length of the left ventricle major axis as a function of time. And when the operator presses the AV DIST button, the UIP 130 will display a plot of the length of the displacements of both the AV plane points as a function of time.

The UIP 130 may obtain the data for the plot from the M&A subsystem, for example, or from data stored in the memories. The imaging system 100 is not limited to the type of plots noted above however. Rather, many other plots may be supported by adding a different button to the plot menu, and adding support in the UIP 130 to display that plot.

Furthermore, the UIP 130 supports creating an average of end-systole volumes and end-diastole volumes for several cardiac cycles. More specifically, the UIP 130 may respond to a cardiac cycle selection input in order to switch to a different cardiac cycle data set. Subsequently, the UIP 130 may proceed as explained above by displaying a new end-diastole and end-systole endocard, and responding to control inputs to adjust the endocards.

When the operator then presses the TRANSFER button, the UIP 130 may then transfer the new end-diastole and end-systole volumes to the worksheet 140. In the worksheet 140, the UIP 130, the M&A subsystem, or another program may average the new volumes with the physiological data already present in the worksheet 140. The UIP 130 may then display the LVEF anywhere on the display.

The UIP 130 supports ventricle analysis not only for apical four chamber views, but also for apical two chamber views. As an example, the operator may begin with B-mode images that show the four chamber view, then proceed to interact with the UIP 130 to adjust the endocards and transfer the volume data to the worksheet 140.

The operator may then again activate the FREEZE button to restart live TVI data acquisition and move the probe 104 to show an apical two chamber view. Subsequently, the operator may then proceed as noted above to adjust any of the physiological markers that the UIP 130 displays, including the ventricle apex markers, AV plane markers, endocards, and the like.

Figure 5:
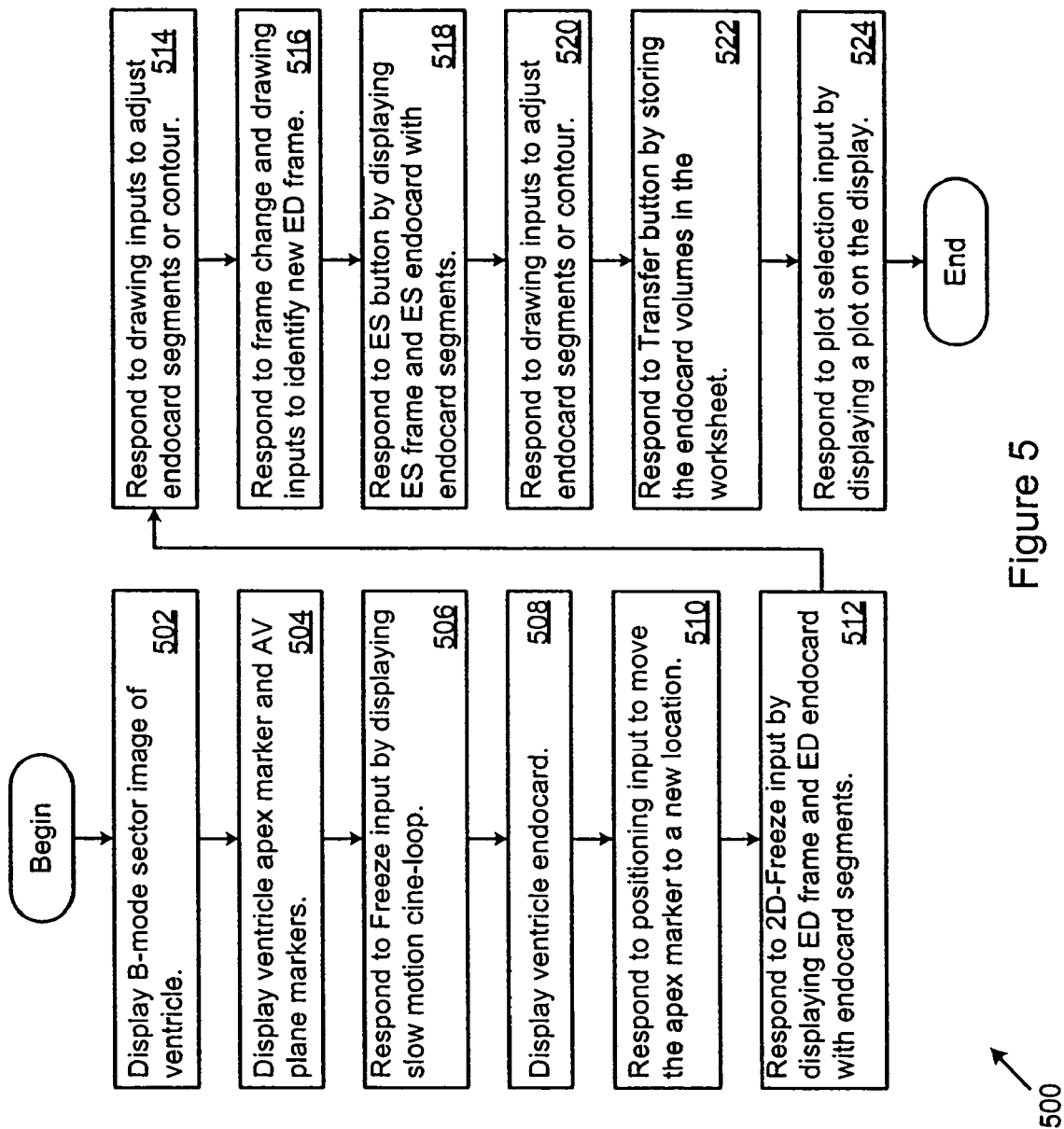
FIG. 5 presents a flow diagram of the steps taken by the user interface in place in the ultrasound imaging system shown in FIG. 1.

With regard next to FIG. 5, that figure shows a flow diagram 500 of the steps taken by the UIP 130 in the imaging system 100. The UIP 130 displays a B-mode sector image 202 of the ventricle (Step 502) as well as a ventricle apex marker 206 and AV plane markers 208 and 210 (Step 504). In one embodiment, the markers 206-210 are displayed responsive to TVI data obtained by the imaging system 100 that helps the M&A subsystem identify those physiological landmarks.

The UIP 130 then responds to the FREEZE button by displaying the B-mode sector images 302 in slow motion (Step 506). At this time, the UIP 130 displays the ventricle endocard 304 detected by the M&A subsystem (Step 508). The operator may provide positioning input (e.g., using a mouse and cursor 308) to select a new position for the ventricle apex 306 that the UIP 130 displays (Step 510). The M&A subsystem may then re-determine the endocard so that it passes through the newly positioned ventricle apex.

The UIP 130 then responds to the 2D-FREEZE input by displaying the end-diastole frame 402, as well as the detected end-diastole endocard 404 with endocard segments 406-408 (Step 512). The operator may then provide drawing inputs that the UIP 130 responds to by adjusting endocard segments or contours as explained above (Step 514).

Note also that operator may provide a frame selection input (e.g., scrolling with a trackball) to scroll to a different frame that the operator believes to be the end-diastole (or end-systole) frame. When the operator subsequently provides drawing inputs on the new frame, the UIP 130 responds by changing the endocard segments or contour, and identifying the new frame as the end-diastole (or end-systole) frame (Step 516).

One the operator has finished with the end-diastole endocard, the operator may then provide an end-diastole to end-systole input (e.g., by clicking on the ES button). The UIP 130 responds by displaying the end-systole frame along with the end-systole endocard and endocard segments (Step 518). As with the end-diastole endocard, the operator may provide drawing inputs that the UIP 130 responds to by adjusting the end-systole endocard segments or contour (Step 520).

When the operator has finished adjusting both endocards, the operator may then provide a completion input (e.g., by pressing the Transfer button). The UIP 130 responds by storing the endocard volumes in the worksheet 140 (Step 522). In addition, the user interface program may display one or more physiological data plots (e.g., a ventricle volume plot) in response to a plot selection input (e.g., clicking on the VOLUME button) (Step 524).

Using the user interface methods and systems described above, doctors and technicians are able to provide control inputs directed to physiological markers (e.g., position inputs directed to ventricle apex and AV plane markers, and drawing inputs directed to endocards) to guide the imaging system 100 in determining physiological definitions for structures such as a ventricle. The imaging system 100 may then make more accurate measurements of physiological parameters, such as the ejection fraction. The user interface provides a less complicated, less time consuming, and less cumbersome way for doctors and technicians to guide and control the measurement and analysis operations provided by the imaging system 100. The imaging system 100 may thereby obtain improved analysis results.

While various embodiments of the invention have been described, it will be apparent to those of ordinary skill in the art that many more embodiments and implementations are possible that are within the scope of this invention.

What is claimed is:

1. A medical imaging system comprising:
   image acquisition circuitry;
   a display;
   a processor coupled to the image acquisition circuitry and the display; and
   a memory coupled to the processor and including a user interface program for causing the processor to perform a method comprising the steps of automatically displaying an initial physiological marker on the display, receiving a control input including an operator drawn line segment; and adjusting the initial physiological marker by combining the operator drawn line segment into the initial physiological marker to generate a modified physiological marker.

2. The medical imaging system of claim 1, where the initial physiological marker is a ventricle endocard.

3. The imaging system of claim 1, where the initial physiological marker is a ventricle endocard comprising endocard segments, and where the operator drawn line segment includes a segment drawing input.

4. The imaging system of claim 3, where the step of adjusting the initial physiological marker comprises the step of replacing at least one of the endocard segments with the operator drawn line segment.

5. The imaging system of claim 1, where the initial physiological marker is a ventricle apex marker.

6. The imaging system of claim 5, where the control input includes a position input.

7. The imaging system of claim 6, where the step of adjusting the initial physiological marker comprises the step of moving the ventricle apex marker in accordance with the control input.

8. The imaging system of claim 1, where the initial physiologic marker is a ventricle end-diastole endocard.

9. The imaging system of claim 8, where the operator drawn line segment includes an end-diastole drawing input and where the step of adjusting the initial physiological marker comprises the step of modifying the ventricle end-diastole endocard in accordance with the operator drawn line segment.

10. The imaging system of claim 9, further comprising receiving a subsequent control input comprising an end-diastole to end-systole switch input.

11. The imaging system of claim 10, further comprising, in response to the end-diastole to end-systole switch input, the step of displaying a subsequent physiological marker on the display, the subsequent physiological marker comprising a ventricle end-systole endocard.

12. The imaging system of claim 11, where the user interface program further causes the processor to perform the steps of receiving an end-systole drawing input and modifying the ventricle end-systole endocard in accordance with the end-systole drawing input.

13. The imaging system of claim 1, where the user interface program further cases the processor to perform the steps of receiving a completion input, and responsively transferring physiological data obtained by the imaging system to a worksheet.

14. The imaging system of claim 13, where the physiological data comprises an end-diastole measurement and an end-systole measurement, and where the worksheet is an Ejection Fraction worksheet.

15. The imaging system of claim 14, where the end-systole measurement is an end-systole volume.

16. The imaging system of claim 14, where the end-diastole measurement is an end-diastole volume.

17. The imaging system of claim 1, where the step of displaying comprises the step of displaying a ventricle apex marker on a B-mode cine-loop.

18. The imaging system of claim 1, where the step of displaying comprises displaying a ventricle apex marker and an atrio-ventricular plane marker.

19. The imaging system of claim 1, where the operator drawn line segment is a manual drawing by a user that replaces a portion of the initial physiological marker.

20. The imaging system of claim 1, where the operator drawn line segment is near the initial physiological marker on the display and adjusting the initial physiological marker includes changing a nearest segment of the initial physiological marker to reflect the operator drawn line segment.

21. The imaging system of claim 1, further comprising an operator input, where the method performed by the processor includes tracking motion of the operator input to determine the operator drawn line segment.

22. The imaging system of claim 21, where the operator drawn line segment is a trace of the motion of the operator input.

23. The imaging system of claim 1, where the adjusting operation of the method performed by the processor includes replacing a line segment of the initial physiological marker with the operator drawn line segment.

* * * * *